US00PP25427P2

(12) United States Plant Patent
Hartman

(10) Patent No.: US PP25,427 P2
(45) Date of Patent: Apr. 7, 2015

(54) ***CALADIUM* PLANT NAMED 'MODERN ART'**

(50) Latin Name: *Caladium×hortulanum*
Varietal Denomination: Modern Art

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 129 days.

(21) Appl. No.: 13/986,554

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Modern Art', characterized by its compact, upright and uniformly mounding plant habit; vigorous growth habit; lance-type leaves that are creamy white to greyed green in color with random dark red-colored spots and blotches, white-colored venation and green-colored margins; and good landscape performance.

4 Drawing Sheets

Botanical designation: *Caladium×hortulanum.*
Cultivar denomination: 'MODERN ART'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Modern Art'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2006 in Avon Park, Fla. of *Caladium×hortulanum* 'Twist and Shout', not patented, as the female, or seed, parent with a proprietary selection of *Caladium×hortulanum* identified as code number WS-02-18, not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2007.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2008 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Modern Art'. These characteristics in combination distinguish 'Modern Art' as a new and distinct *Caladium* plant:

1. Compact, upright and uniformly mounding plant habit.
2. Vigorous growth habit.
3. Lance-type leaves that are creamy white to greyed green in color with random dark red-colored spots and blotches, white-colored venation and green-colored margins.
4. Good landscape performance.

Plants of the new *Caladium* differ primarily from plants of the female parent, 'Twist and Shout', in leaf color as plants of 'Twist and Shout' have leaves that are olive green in color with coppery orange-colored blotches. In addition, plants of the new *Caladium* grow slower and produce finished plants two to three weeks later than plants of 'Twist and Shout'.

Plants of the new *Caladium* differ primarily from plants of the male parent selection in leaf color as leaves of plants of the male parent selection are white and greyed white in color with a variable pink-colored blush and green-colored margins. In addition, plants of the new *Caladium* and the male parent selection differ in leaf petiole color as plants of the male parent selection have green-colored leaf petioles with dark green-colored stippling and streaks.

Plants of the new *Caladium* can be compared to plants of *Caladium×hortulanum* 'Gingerland', not patented. In side-by-side comparisons, plants of the new *Caladium* differed primarily from plants of 'Gingerland' in leaf coloration as leaves of plants of 'Gingerland' were white in color with red purple-colored speckling, dark red-colored spots and green-colored margins. In addition, plants of the new *Caladium* and 'Gingerland' differed in leaf petiole coloration as leaf petioles of plants of 'Gingerland' were tan pink to tan green with darker green-colored stippling, streaks and tessellations.

Plants of the new *Caladium* can be compared to plants of *Caladium×hortulanum* 'Candyland', disclosed in U.S. Plant Pat. No. 18,766. In side-by-side comparisons, plants of the new *Caladium* differed primarily from plants of 'Candyland' in the following characteristics:

1. Plants of the new *Caladium* were more compact than plants of 'Candyland'.
2. Plants of the new *Caladium* grew slower and produced finished plants about one to two weeks later than plants of 'Candyland'.
3. Plants of the new *Caladium* and 'Candyland' differed in leaf coloration as leaves of plants of 'Candyland' were white to grey-green in color with random pink-colored spots and green-colored margins.
4. Plants of the *Caladium* and 'Candyland' differed in leaf petiole coloration as leaf petioles of plants of 'Candyland' were tan pink in color with darker-colored stippling, streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Modern Art' in a 15-cm container and grown in a shadehouse.

The photograph on the second sheet is a comparison view of typical plants of 'Modern Art' grown in 15-cm containers; the plant on the left has not had its tuber de-eyed and the plant on the right has had its tuber de-eyed prior to planting.

The photograph at the top of the third is a close-up view of a typical freshly-harvested tuber and roots of 'Modern Art'.

The photograph at the bottom of the third sheet is a close-up view of a typical inflorescence of 'Modern Art'.

The photograph at the top of the fourth sheet is a comparison view of typical potted plants of 'Candyland' (left), 'Modern Art' (center) and 'Gingerland' (right).

The photograph at the bottom of the fourth sheet is a comparison view of typical potted plants of the male parent selection (left), 'Modern Art' (center) and the female parent, 'Twist and Shout' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Modern Art'.

Parentage:

*Female, or seed, parent.*—*Caladium×hortulanum* 'Twist and Shout', not patented.

*Male, or pollen, parent.*—Proprietary selection of *Caladium×hortulanum* identified as code number WS-02-18, not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments elliptic in shape. Height: About 3.7 cm. Diameter: About 4.7 cm. Segment height: About 2.5 cm. Segment diameter: About 2.4 cm. Texture: Thick, starchy; somewhat brittle. Color: Epidermis, freshly-harvested: Close to 199A to 199B and N199B. Epidermis, dried: Close to 200A to 200B. Cortical tissue: Close to 2D. Axillary buds: Close to 27C. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounding plant habit; vigorous and dense growth habit; potted plants in finished or saleable form in about eight to nine weeks after planting tubers; leaf petioles and leaves arise from one or more growing points on tubers; petioles mostly upright and arching outwardly with development.

*Plant height, from soil level to top of foliar plane, shadehouse-grown potted plants.*—About 26 cm to 33 cm.

*Plant height, from soil level to top of inflorescences, shadehouse-grown potted plants.*—About 41.5 cm.

*Plant diameter or spread, shadehouse-grown potted plants.*—About 37 cm to 42 cm.

*Number of clumps per plant, shadehouse-grown potted plants.*—About three from de-eyed tubers.

*Cataphylls, shadehouse-grown potted plants.*—Length: About 5 cm to 15.5 cm. Width: About 1 cm to 2 cm. Shape: Wedge-shaped. Apex: Acute to acuminate. Base: Sheathing the stem. Color, outer surface: Close to N170D and 197C variably streaked with close to N200A and 197A; with development, color becoming closer to 200A stained with close to 187A to 187B. Color, inner surface: Close to N155C; outer surface colors and patterns visible.

Foliage description:

*Arrangement and type.*—Alternate; simple; lance-type.

*Length, shadehouse-grown potted plants.*—About 18.5 cm to 27 cm.

*Width, shadehouse-grown potted plants, flattened.*—About 12 cm to 19 cm.

*Shape.*—Ovate.

*Apex.*—Acuminate to acute.

*Base.*—Sagittate to sagittate peltate.

*Margin*.—Entire; somewhat wavy with broad undulations.

*Texture, upper surface*.—Smooth, glabrous; leathery; dull sheen.

*Texture, lower surface*.—Smooth, glabrous; glaucous.

*Venation pattern*.—Pinnate.

*Color, shadehouse-grown potted plants*.—Developing leaves, upper surface: Background color: Central areas, close to 193C, 194C and 147D; random spots and blotches, close to 183A; marginal areas, close to 147A and 194C. Basal notch: Close to 187A to 187B. Venation: Close to 193A. Developing leaves, lower surface: Background color: Central areas, close to 191A; random spots and blotches, close to 182B to 182C and 183C; margins, close to 187A. Basal notch: Close to 187A. Venation: Close to 194B; adjacent to venation, close to 157B. Fully expanded leaves, upper surface: Background color: Central areas, close to 193B to 193C and 194B; random spots and blotches, close to 183A and 184A to 184B; marginal areas, close to 147A to 147B and 194C. Basal notch: Close to 187A. Midvein: Close to 193D. Primary venation: Close to 193A to 193B. Fully expanded leaves, lower surface: Background color: Central areas, close to 157B and 147D, random spots and blotches, close to 182B to 182C and 183C; margins, close to 191A tinged with close to N186C; margin, close to 187A. Basal notch: Close to 187A. Midvein: Close to 147D tinged with close to 162D. Primary venation: Close to 147C; adjacent to venation, close to 157B.

*Petiole*.—Aspect: Initially upright and straight; with development, leaning outwardly; flexible. Length, shadehouse-grown potted plants: About 20 cm to 29.5 cm. Diameter, distal, shadehouse-grown potted plants: About 3.5 mm to 6 mm. Diameter, proximal, shadehouse-grown potted plants: About 7 mm to 11 mm. Color, shadehouse-grown potted plants: Close to 147A to 147C faintly stippled and streaked with close to 199A. Wing length, shadehouse-grown potted plants: About 6 cm to 8.5 cm. Wing diameter, shadehouse-grown potted plants: About 6 mm to 10.5 mm. Wing color, shadehouse-grown potted plants, outer surface: Close to 147C tinged with close to 146C and variably stippled and streaked with close to 147A to 147B. Wing color, shadehouse-grown potted plants, inner surface: Close to N155C, distally tinged with close to 182D; outer surface colors and patterns visible.

Inflorescence description: Inflorescences observed on eight week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; sweet jasmine-like fragrance with camphor-like notes.

*Natural flowering season and flower longevity*.—Plants of the new *Caladium* typically flower during the spring or early summer in central Florida; flowers develop about eight weeks after growth commences; inflorescences last about three days before fading; inflorescences persistent.

*Spathe*.—Length, overall: About 14 cm. Length, distal open portion: About 10 cm. Length, proximal closed portion: About 4 cm. Width, distal open portion: About 3.8 cm. Width, at constriction: About 1.6 cm. Width, proximal closed portion: About 2.9 cm. Shape: Obovate. Apex: Acuminate. Base: Tapering to the peduncle. Margin: Entire, slightly reflexed. Texture, front and rear surfaces: Smooth, glabrous. Color, front surface: Distal open portion: Close to 155A, variable occasional streaks and spots of close to 183C to 183D and 147D; with development, color becoming closer to 200D. Proximal closed portion: Close to 138C to 138D and 147D, with small flecks, close to 187A, and larger sectors, close to 187B; color does not change with development. Color, rear surface: Distal open portion: Close to 157B and 16D, variably and faintly tinged with close to 182B, and with occasional sectors, close to 147C and 146C. Proximal closed portion: Close to 146A with streaks and sectors, close to 146B.

*Spadix*.—Length: About 11.5 cm. Length, male flower zone: About 9.4 cm. Length, sterile zone: About 1.4 cm. Length, female flower zone: About 2.1 cm. Diameter, male flower zone: About 1.2 cm. Diameter, sterile flower zone: About 1 cm. Diameter, female flower zone: About 1.1 cm. Shape: Columnar, spindle-shaped. Apex: Bluntly acute. Base: Obtuse. Aspect: Upright. Color, mature, male zone: Close to 159D. Color, mature, sterile zone: Close to 159D. Color, mature, female zone: Close to N170D. Male flowers: Quantity per spadix: About 198. Shape: Obovate. Height: About 3 mm. Diameter: About 3 mm to 4 mm. Pollen amount: Moderate. Pollen color: Close to 4C. Female flowers: Quantity per spadix: About 145. Shape: Obovate. Height: About 3 mm. Diameter: About 1.5 mm. Stigma color: Close to N170D. Ovary color: Close to 155C.

*Scape*.—Length: About 27.5 cm. Diameter: About 8 mm. Strength: Sturdy; flexible. Aspect: Mostly erect. Texture: Smooth, glabrous; glaucous. Color: Close to 147B tinged with close to 146B.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Modern Art' as illustrated and described.

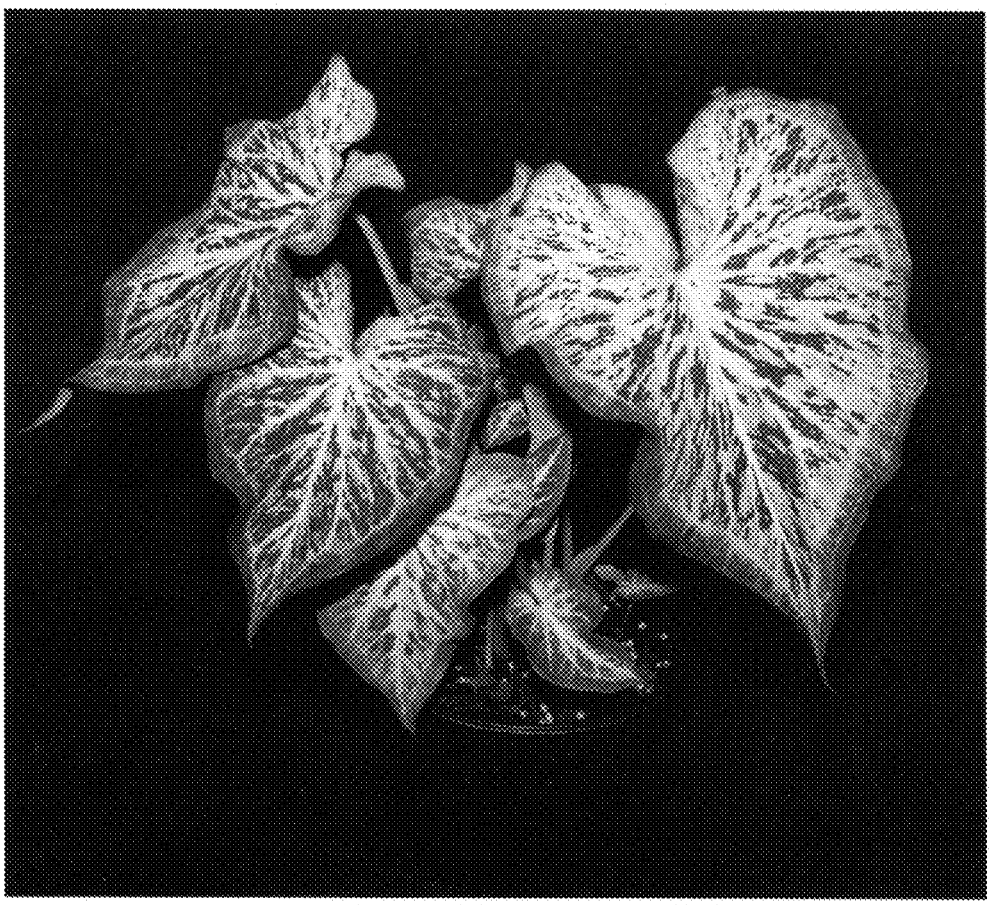

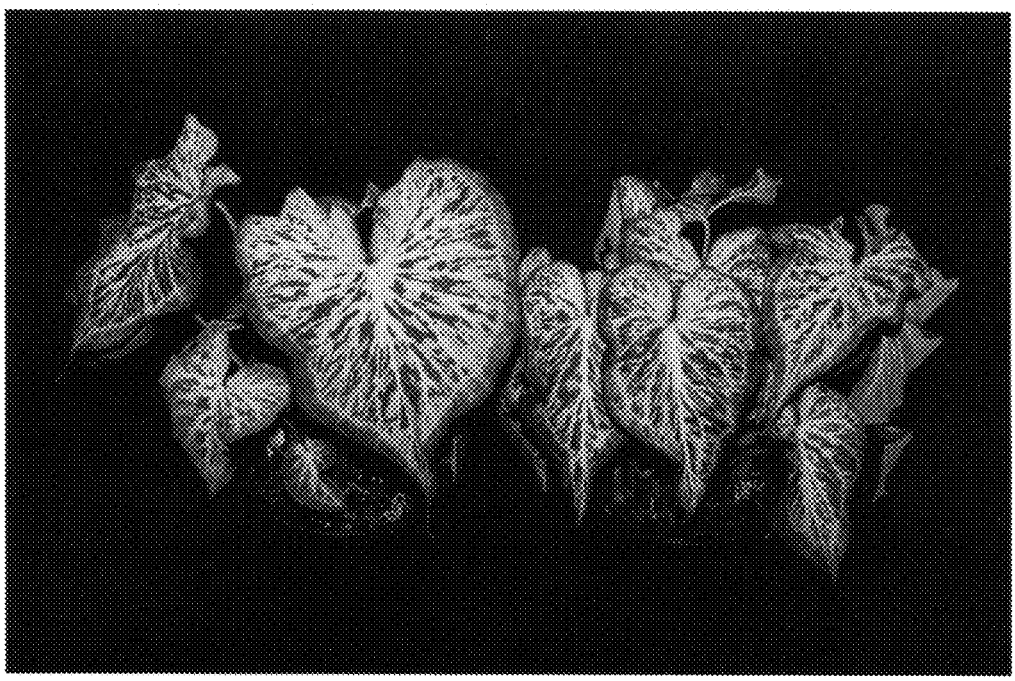

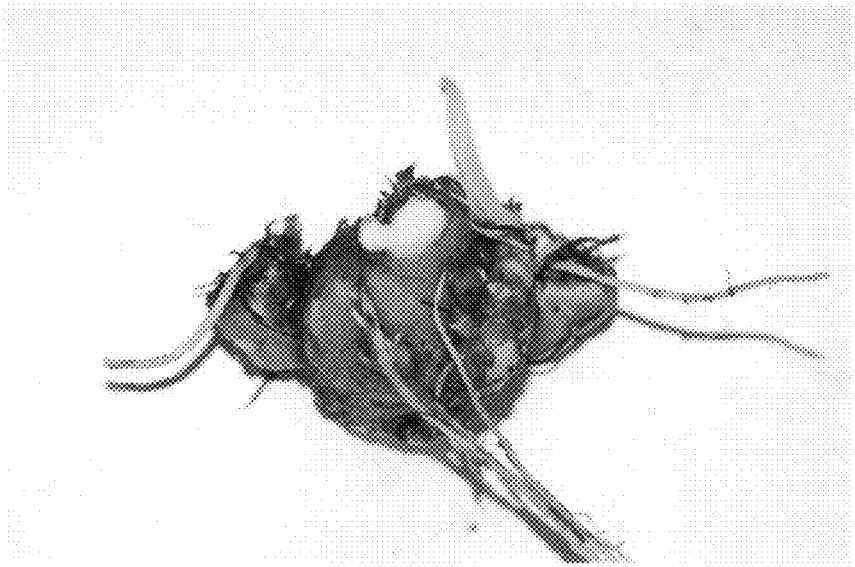
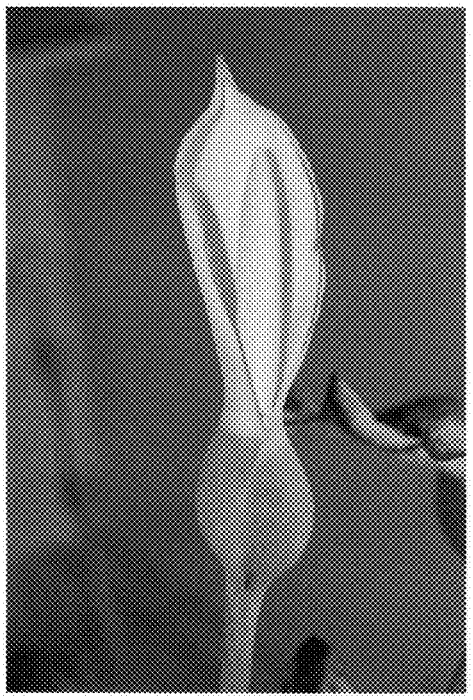

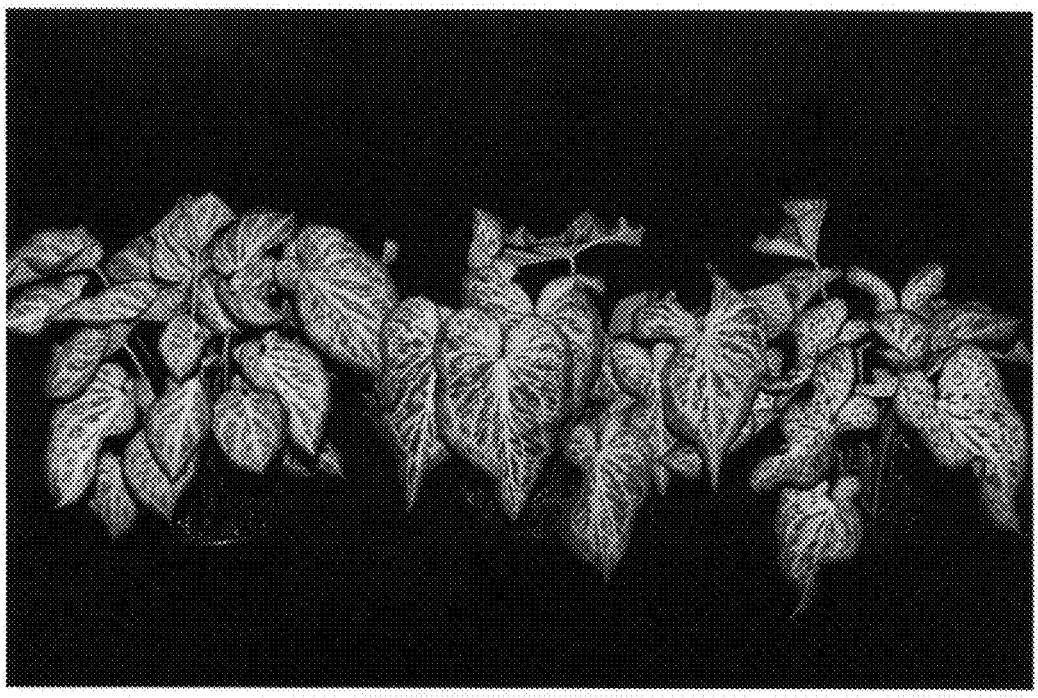
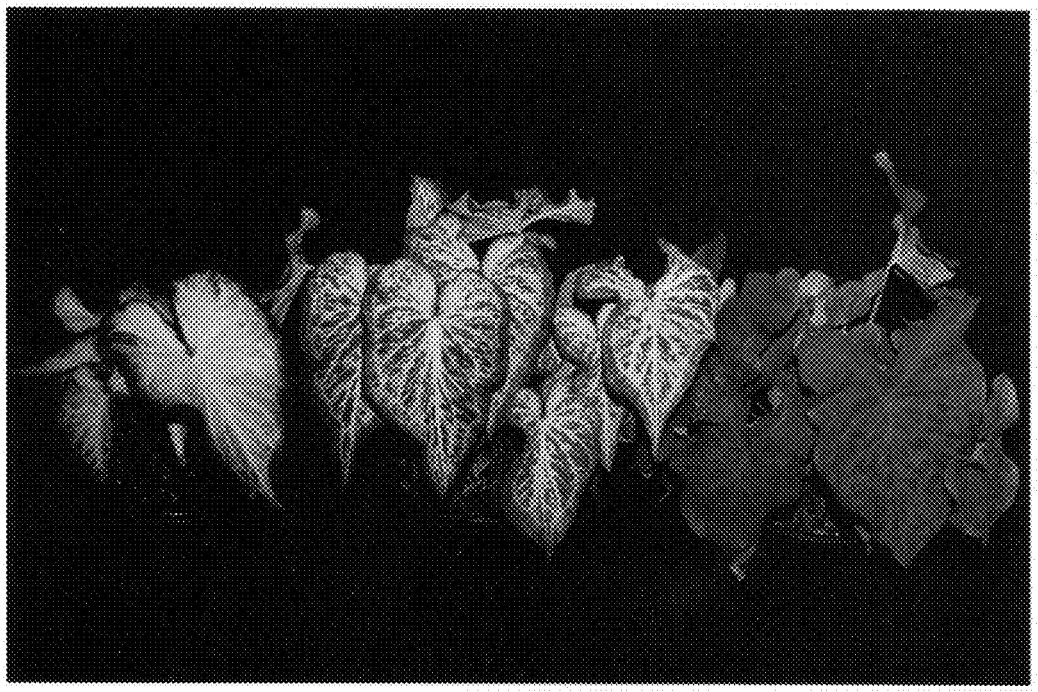

* * * * *